United States Patent [19]

Driscoll

[11] Patent Number: 5,068,181

[45] Date of Patent: Nov. 26, 1991

[54] METHOD OF MONITORING REAGENT DELIVERY IN A SCANNING SPECTROPHOTOMETER

[75] Inventor: Richard C. Driscoll, Raleigh, N.C.

[73] Assignee: Akzo N.V., Arnhem, Netherlands

[21] Appl. No.: 443,953

[22] Filed: Dec. 1, 1989

[51] Int. Cl.$^5$ .................... G01N 21/77; N01N 21/78
[52] U.S. Cl. ........................................ 435/13; 436/56; 436/69; 436/164; 436/166; 436/172; 436/800; 356/39
[58] Field of Search ................. 436/164, 166, 800, 56, 436/42, 69, 172, 15; 435/13; 356/407, 39

[56] References Cited

U.S. PATENT DOCUMENTS 4,204,839  5/1980  Wu et al. ........................ 23/230 B
4,329,149  5/1982  Schoonover et al. ............ 23/230 R Primary Examiner—David L. Lacey
Assistant Examiner—David Redding
Attorney, Agent, or Firm—Spencer & Frank

[57] ABSTRACT

A method for measuring the concentration of a reagent in a reaction mixture including the steps of: adding dye to a reagent until the dye is at a given concentration in the reagent; mixing the reagent with a reaction mixture comprising a sample which reacts with the reagent to form a reaction product; measuring the formation of reaction product at a first spectral region; measuring the concentration of dye in the reaction mixture at a second spectral region in which the dye has an optical characteristic such as absorption or fluorescence, the second spectral region being different from the first spectral region; and determining the concentration of the reagent in the reaction mixture based on the concentration of dye measured.

In a further aspect of the invention there is provided a reagent containing a dye useful in the above method.

17 Claims, 1 Drawing Sheet

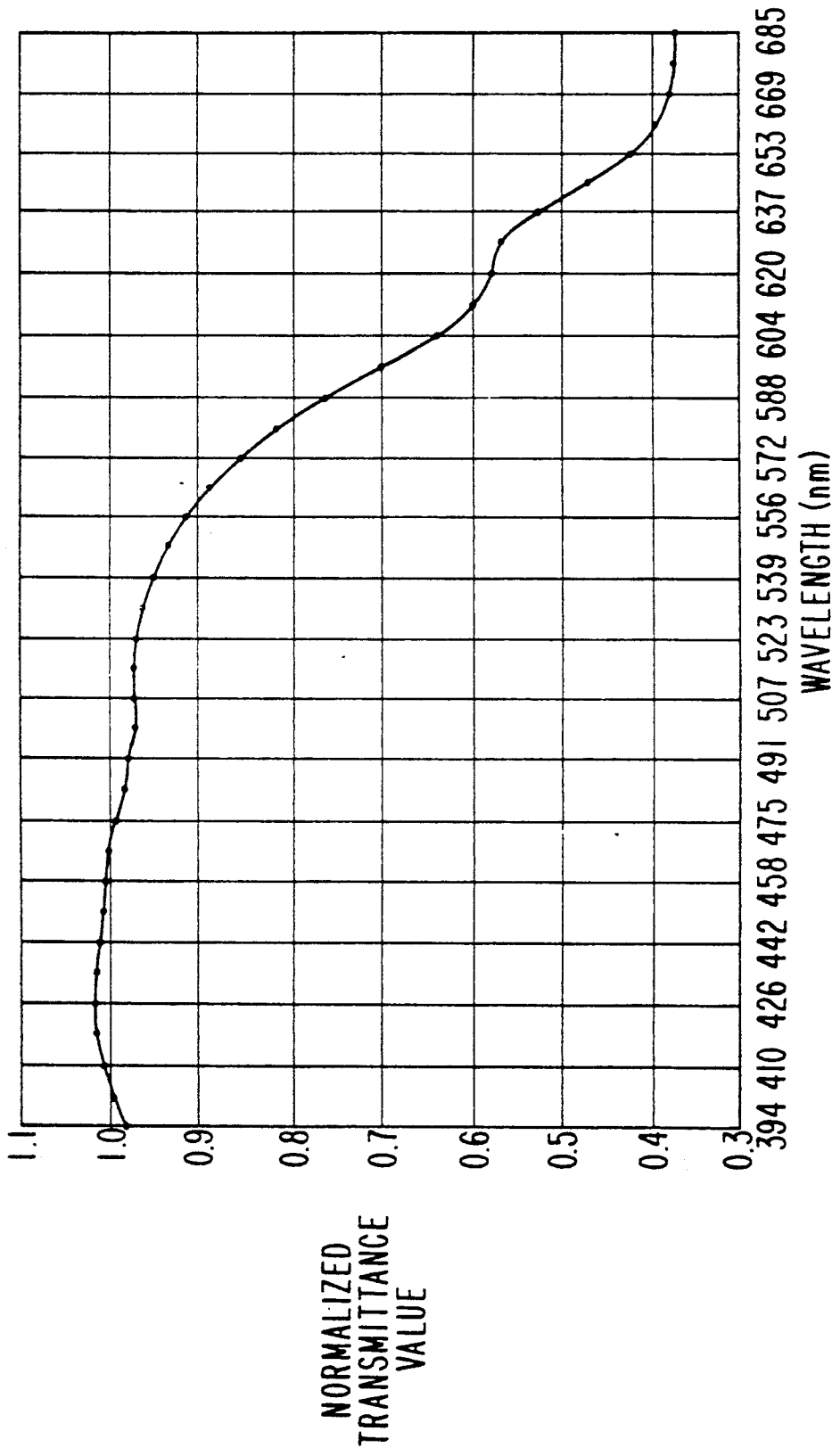

5,068,181

METHOD OF MONITORING REAGENT DELIVERY IN A SCANNING SPECTROPHOTOMETER

BACKGROUND OF THE INVENTION

The present invention relates to a method for monitoring reagent delivery in a scanning spectrophotometer and a reagent useful in such a method.

A problem in current reagent delivery systems is that once a reagent has been added to a reaction mixture, it is difficult to determine the actual amount of the reagent present in the reaction mixture. This is a particular problem in blood coagulation assays. In this type of assay, when a blood coagulating reagent such as thromboplastin or thrombin is aspirated into a pipette, air may be drawn into the pipette, so that an insufficient amount of the reagent may be dispensed.

Another problem with assays of the above type is that it may not be possible to easily determine whether there is a plasma sample to be tested present in the reaction cuvette.

SUMMARY OF THE INVENTION

Therefore, it is an object of the present invention to provide a method for accurately measuring the amount of reagent dispensed into a reaction mixture.

It is another object of the invention to provide a method for determining whether the sample to be tested is present in the reaction mixture.

It is yet another object of the invention to provide a reagent useful in the above method.

The invention provides a method for measuring the concentration of a reagent in a reaction mixture including the steps of: adding dye to a reagent until the dye is at a known concentration in the reagent; mixing the reagent with a reaction mixture comprising a sample which reacts with the reagent to form a reaction product; measuring the formation of reaction product at a first spectral region; measuring the concentration of dye in the reaction mixture at a second spectral region in which the dye has an optical characteristic such as absorption or fluorescence, the second spectral region being different from the first spectral region; and determining the concentration of the reagent in the reaction mixture based on the concentration of dye measured.

In another embodiment, the invention provides a blood coagulating reagent containing a dye which has an optical characteristic in a spectral region outside a reaction mixture's region of interest.

BRIEF DESCRIPTION OF THE DRAWING

FIG. 1 illustrates the spectrum of methylene blue, a dye useful in practicing the invention.

DESCRIPTION OF THE PREFERRED EMBODIMENTS

The present method is preferably used in conjunction with an optical monitoring system such as that disclosed in concurrently commonly assigned filed U.S. patent application Ser. No. 443,952, now U.S. Pat. No. 5,002,392 to Swope et al., entitled "Multichannel Optical Monitoring System", the disclosure of which is incorporated herein by reference. Various fluid reagents are mixed with the sample in a cuvette to form a reaction mixture the optical characteristics of which are monitored. The system is principally used to conduct tests on blood plasma, such as tests involving the addition of thromboplastin or thrombin in order to convert fibrinogen to fibrin.

In the present invention, a known amount of dye is added to a known amount of one of the reagents to be added to the reaction mixture. The concentration of dye in the reagent is preferably about 1 part per thousand. Preferably, the dye is added to a blood coagulation reagent such as thromboplastin or thrombin, but the dye may be added to other reagents in a clotting or other reaction.

The dye which is added to the blood coagulating reagent has the optical characteristic of either absorbing light at a given wavelength or fluorescing light of a given wavelength. Whichever optical characteristic the dye has, the dye should be compatible with the contents of the reaction mixture and have an optical characteristic in a spectral region that is outside the reaction mixture's region of interest, the region in which the measurement of the formation of reaction product is made.

For example, when the reagent is a blood coagulating agent such as thrombin or thromboplastin and the reaction mixture is a coagulation assay, an appropriate light absorbing dye, such as a blue dye, may be added to the thrombin before adding the thrombin to the plasma being tested. A preferred dye for this purpose is methylene blue (3,9-bis-methyl-amino-phenazo-thionium chloride; methyl thionine chloride) which has a spectrum as shown in FIG. 1. As can be seen from this spectrum, methylene blue has a large transmittance and therefore a low absorption in the range 400–550 nm, the region in which clotting of blood in a coagulation assay is typically monitored by a spectrophotometer, but has a high absorption in the range of 653–685 nm. While the exact range of absorption of the dye is not critical, preferably the dye does not absorb significantly in the region of 400–550 nm and does absorb significantly in a range outside of this region.

By monitoring the concentration of dye in the reaction mixture at a wavelength at which it absorbs, the concentration of the thrombin in the reaction mixture can be determined. An indication of too much absorption at the dye's wavelength indicates that the thrombin has not been sufficiently diluted before adding the thrombin to the plasma or that there is no plasma present in the reaction mixture or present in the correct proportions. In contrast, too little absorption at the dye's wavelength indicates either that not enough thrombin has been added or that there is too much plasma present in the reaction mixture.

If either too much or too little absorption is measured by the spectrophotometer at the dye's wavelength, the spectrophotometer by means of a display or print-out warns the operator of the problem. By adding a suitable dye to any of the reagents and then monitoring the absorption at an appropriate wavelength for a short time after delivery of the reagent, the amount of reagent plus plasma can be estimated well enough to know whether the plasma and reagent are both present in the reaction mixture.

While the above description has been of a specific reagent and reaction mixture, the invention may be practiced with other suitable reagents and reaction mixtures. Further, the addition of more than one reagent may be monitored by adding dyes having different principal absorption wavelengths to the reagents and monitoring the concentration of each of the dyes in the reaction mixture.

In a manner similar to that discussed above for a light absorbing dye, a dye which fluoresces light in a region outside the region of interest for the reaction mixture may be added to a blood coagulating agent. When a fluorescent dye is used instead of a light absorbing dye, the concentration of reagent is monitored by measuring the presence of light at a particular wavelength due to fluorescence. A suitable fluorescent dye for this purpose is rhodamine B which fluoresces in the red region of the spectrum. While the fluorescent dye preferably does not absorb light significantly in the reaction mixture's region of interest, it may absorb light at any wavelength of the spectrum.

It will be understood that the above description of the present invention is susceptible to various modifications, changes and adaptations, and the same are intended to be comprehended within the meaning and range of equivalents of the appended claims.

What is claimed is:

1. A method for measuring the concentration of thromboplastin in a reaction mixture comprising the steps of:
    adding dye to thromboplastin until the dye is at given concentration in the thromboplastin;
    mixing the thromboplastin with a reaction mixture comprising a blood plasma sample which reacts with the thromboplastin to form a reaction product;
    measuring the formation of the reaction product at a first spectral region;
    measuring the concentration of dye in the reaction mixture at a second spectral region in which the dye has an optical characteristic, the second spectral region being different from the first spectral region; and
    determining the concentration of the thromboplastin in the reaction mixture based on the concentration of dye measured.

2. The method of claim 1, wherein the dye absorbs light in the second spectral region.

3. The method of claim 2, wherein the dye does not substantially absorb light in the first spectral region.

4. The method of claim 1, wherein the dye comprises methylene blue and the second spectral region is in the range of about 653–685 nm.

5. The method of claim 1, wherein the dye fluoresces light in the second spectral region.

6. The method of claim 1, wherein the dye comprises rhodamine B.

7. The method of claim 1, further comprising determining whether blood plasma has been added to the reaction mixture based on the concentration of dye in the reaction mixture.

8. The method of claim 1, wherein the added dye is at a concentration of about 1 part per thousand of the reagent.

9. A method for measuring the concentration of a thrombin in a reaction mixture comprising the steps of:
    adding dye to thrombin until the dye is at given concentration in the thrombin;
    mixing the thrombin with a reaction mixture comprising a blood plasma sample which reacts with the reagent to form a reaction product;
    measuring the formation of the reaction product at a first spectral region;
    measuring the concentration of dye in the reaction mixture at a second spectral region in which the dye has an optical characteristic, the second spectral region being different from the first spectral region; and
    determining the concentration of the thrombin in the reaction mixture based on the concentration of dye measured.

10. The method of claim 9, wherein the dye absorbs light in the second spectral region.

11. The method of claim 9, wherein the dye does not substantially absorb light in the first spectral region.

12. The method of claim 9, wherein the dye comprises methylene blue and the second spectral region is in the range of about 653–685 nm.

13. The method of claim 9, wherein the dye fluoresces light in the second spectral region.

14. The method of claim 9, wherein the dye comprises rhodamine B.

15. The method of claim 9, further comprising determining whether blood plasma has been added to the reaction mixture based on the concentration of dye in the reaction mixture.

16. The method of claim 9, wherein the added dye is at a concentration of about 1 part per thousand of the reagent.

17. A method for measuring the concentration of a reagent in a reaction mixture comprising the steps of:
    adding rhodamine B to a reagent until the rhodamine B is at given concentration in the reagent;
    mixing the reagent with a reaction mixture comprising a biological sample which reacts with the reagent to form a reaction product;
    measuring the formation of the reaction product at a first spectral region;
    measuring the concentration of rhodamine B in the reaction mixture at a second spectral region in which the rhodamine B fluoresces, the second spectral region being different from the first spectral region; and
    determining the concentration of the reagent in the reaction mixture based on the concentration of rhodamine B measured.

* * * * *